US005722287A

United States Patent [19]
Forstein

[11] Patent Number: 5,722,287
[45] Date of Patent: Mar. 3, 1998

[54] VIDEO PEDOBAROGRAPH SYSTEM

[76] Inventor: Micah Aaron Forstein, 1900 Dracena Dr., #3, Los Angeles, Calif. 90027

[21] Appl. No.: 456,159

[22] Filed: May 31, 1995

[51] Int. Cl.$^6$ .......................... A61B 5/103; H01C 10/10; H04N 5/08
[52] U.S. Cl. .......................................................... 73/172
[58] Field of Search ................................ 73/172; 128/779

[56] References Cited

U.S. PATENT DOCUMENTS

| | | | |
|---|---|---|---|
| 4,267,728 | 5/1981 | Manley et al. | 73/172 |
| 4,679,075 | 7/1987 | Williams et al. | |
| 4,956,628 | 9/1990 | Furlong | 340/323 |
| 5,010,774 | 4/1991 | Kikuo et al. | 73/172 X |
| 5,068,717 | 11/1991 | Jenison | |
| 5,253,656 | 10/1993 | Rincoe et al. | 73/172 X |
| 5,287,183 | 2/1994 | Thomas et al. | 374/123 X |
| 5,323,650 | 6/1994 | Fullen et al. | 73/172 |
| 5,485,220 | 1/1996 | McNeilly et al. | |
| 5,533,139 | 7/1996 | Parker et al. | |

OTHER PUBLICATIONS

Morlock, Michael M. "*The Use of Pressure Distribution*", Hospital Management International '91, pp. 336–338, 1991.
Solomon, E.G. et al. "The Measurement and display of foot/ground forces during gait", Conference Proceedings of the New Eng. (NE) Bio. Conf., NY., pp. 523–525.

*Primary Examiner*—William A. Cuchlinski, Jr.
*Assistant Examiner*—Willie Morris Worth
*Attorney, Agent, or Firm*—Oppenheimer Poms Smith

[57] ABSTRACT

A video pedobarograph system for providing a real time, qualitative display of dynamic relative pressure measurements includes a plurality of force sensors, a substantially rigid support structure and video pedobarograph electronics. The force sensors generate dynamic relative pressure signals and are positioned within a force sensor matrix structure. The substantially rigid support structure includes a substantially planer surface to which the sensor matrix structure is fixedly secured. The video pedobarograph electronics include a video sync stripper and control logic. The video sync stripper strips a video sync signal from a composite video signal received by the video pedobarograph electronics. The control logic maps the dynamic relative pressure signals to the composite video in response to the video sync signal to generate a mapped composite video signal providing a qualitative display of the dynamic relative pressure signals within a predetermined portion of an overall video image generated from the mapped composite video signal.

22 Claims, 4 Drawing Sheets

1

VIDEO PEDOBAROGRAPH SYSTEM

BACKGROUND OF THE INVENTION

1. Field of the Invention

The present invention relates to a video pedobarograph or foot pressure measuring and display system and, more particularly, a video pedobarograph system for providing a real time, qualitative display of dynamic relative pressure measurements.

2. Description of the Related Art

Generally, pedobarograph systems include a data acquisition system (DAS), a data processor and a computer video monitor. A substantial amount of computer processing overhead is typically dedicated to storing and manipulating sensor output data for display at the computer video monitor. Such prior art systems are principally concerned with processing sensor output data with elaborate algorithms for the purpose of providing a quantitative (e.g., time averaged) display. These systems are relatively costly, in the order of tens of thousands of dollars per system.

Other prior art systems are exemplified by U.S. Pat. No. 5,323,650 to Fullen et al. which discloses a system with a CPU for receiving and processing the output signals of a force sensor array to drive an audible enunciator.

The art is still without a video pedobarograph system for providing a real time, qualitative display of dynamic relative pressure measurements.

Accordingly, an object of the present invention is to provide a video pedobarograph system which provides a real time, qualitative display of dynamic relative pressure measurements by directly mapping indicia of the pressure measurements to a composite video signal.

Another object is to provide a video pedobarograph system which is simply and economically manufactured to meet the particular and limited needs of the clinician.

SUMMARY OF THE INVENTION

In accordance with a specific illustrative embodiment of the present invention, a video pedobarograph system or video foot pressure measuring and display system for directly providing indicia of dynamic relative pressure measurements to a composite video signal includes a plurality of force sensors and video pedobarograph electronics. The plurality of force sensors generate dynamic relative pressure signals. The video pedobarograph electronics receive and map the dynamic relative pressure signals to a composite video signal in real time to generate a mapped composite video signal with visible indicia of the dynamic relative pressure signals.

In a further aspect of the present invention, the video pedobarograph system further includes a substantially rigid support structure to which the plurality of force sensors are fixedly secured. The plurality of force sensors are arranged in a matrix substantially within a force sensor plane.

In still a further aspect of the present invention, a video pedobarograph system for providing a real time, qualitative display of dynamic relative pressure measurements includes a plurality of force sensors which are formed or positioned within a force sensor matrix structure. The video pedobarograph electronics include a video sync stripper and control logic. The video sync stripper strips or derives a video sync signal from the composite video signal. The control logic maps the dynamic relative pressure signals to the composite video in response to the video sync signal. The video pedobarograph electronics generate a mapped composite video signal to provide a qualitative display of the dynamic relative pressure signals within a predetermined portion of an overall video image generated from the mapped composite video signal.

DESCRIPTION OF THE DRAWINGS

Other objects, features and advantages of the invention will become readily apparent upon reference to the following detailed description when considered in conjunction with the accompanying drawings, in which like reference numerals designate like parts throughout the figures thereof, and wherein.

DETAILED DESCRIPTION OF THE PREFERRED EMBODIMENTS

Figure 1:
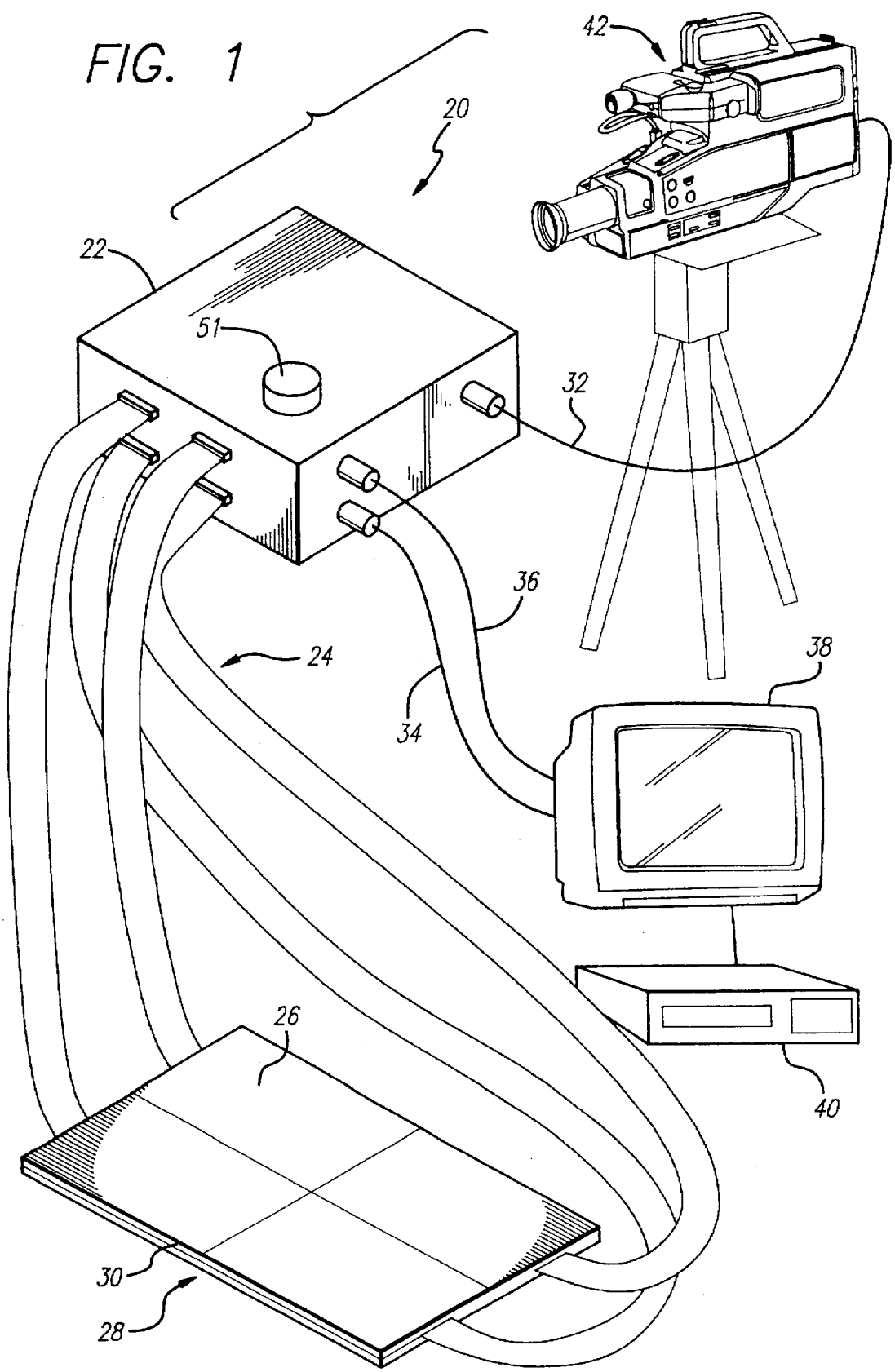
FIG. 1 is a schematic perspective view of a video pedobarograph system illustrating the principles of the present invention.

FIG. 1 shows a video pedobarograph system 20 which includes electronics (not shown) within a housing 22. Cables 24 which are preferably ribbon cables electrically connect the circuitry within the housing 22 to a force sensor matrix structure 26. A plurality of force sensors are formed or positioned within the force sensor matrix structure 26. The force sensors are preferably arranged relative to each other within the force sensor matrix structure 26 in the form of a two dimensional array with at least 1,024 individual pressure sensors. A preferred force sensitive matrix includes four Model #350 256 Zone Matrix Arrays which are manufactured by Interlink Electronics of Carpenteria, Calif. The force sensors in the Interlink matrices comprise Force Sensing Resistors™ (FSR™).

The video pedobarograph system 20 also includes a substantially rigid support structure 28 with a substantially planar surface 30 to which the force sensor matrix structure 26 is fixedly secured. With the force sensor matrix structure 26 secured as such, the plurality of force sensors are arranged in a matrix substantially within a force sensor plane. Accordingly, the force sensors will not slip in position relative to each other and are optimally configured to generate dynamic relative pressure signals in response to applied forces. The dynamic relative pressure signals represent a dynamic relative force measurement over a predetermined area.

Alternatively, the plurality of force sensors may be individually secured to the substantially rigid support structure 28. Furthermore, each sensor mat has a thickness of approximately 20 mils which advantageously allows the gait of a person walking across the sensor matrix structure 26 to be unaffected.

Generally, the video pedobarograph system 20 receives a composite video signal at line 32 and generates a mapped composite video signal at line 34. The mapped composite signal may, for example, comprise a Video Graphics Adapter (VGA) or Super Video Graphics Adapter (SVGA) signal. The mapped composite video signal and an external sync out signal at line 36 are provided to a video display 38. FIG. 1 also shows that a VCR 40 may be electronically connected to receive the mapped composite video signal from an appropriate terminal at the video monitor 38 or, alternatively, directly from line 34 (not shown).

Figure 2:
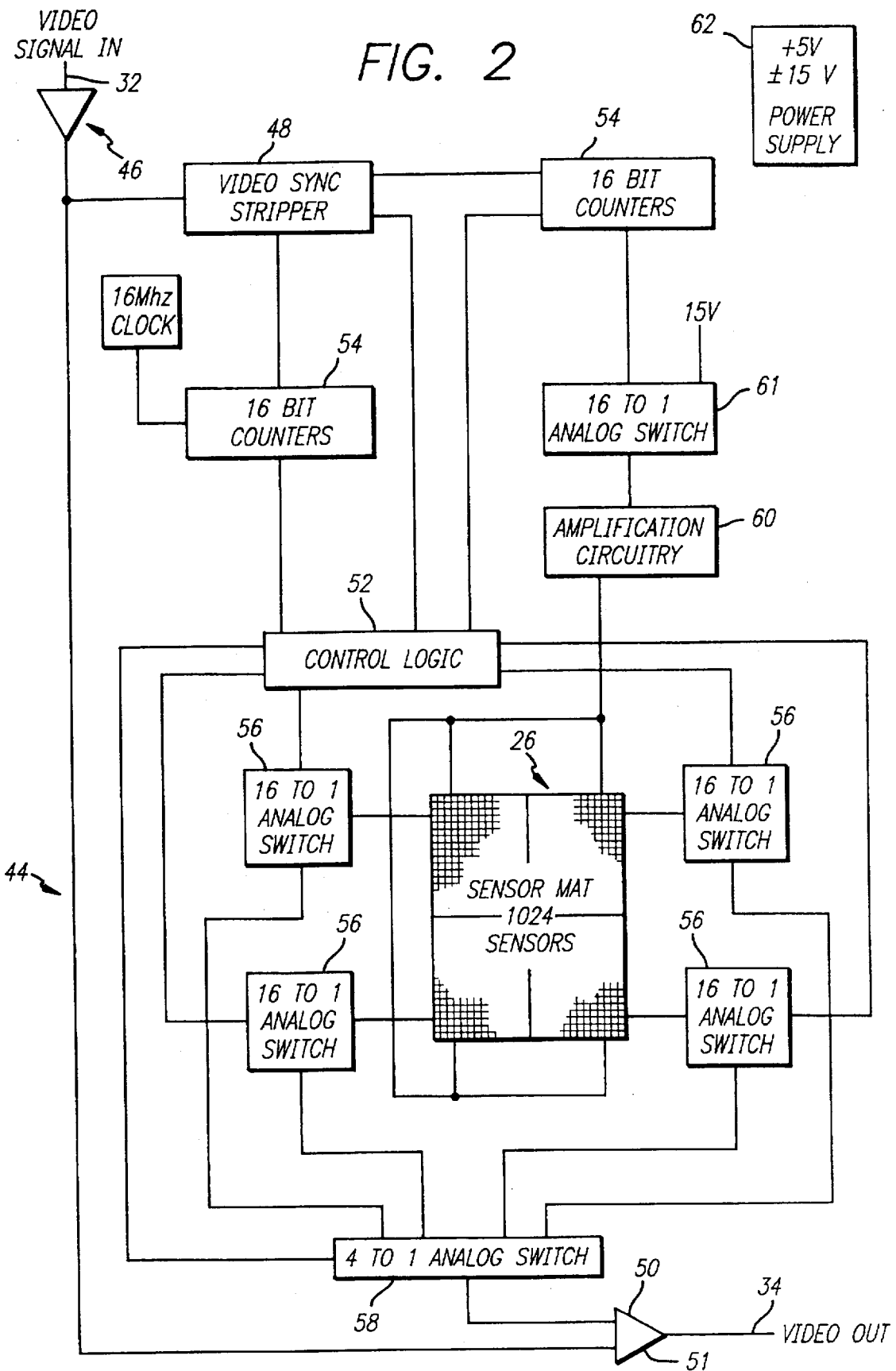
FIG. 2 is a functional block diagram of the plurality of force sensors and the video pedobarograph electronics.

In a first preferred embodiment shown in FIGS. 1 and 2, an external video source 42 is provided. The video in signal at line 32 may be blank video or a video image of a person walking across or standing on the force sensor matrix structure 26. As discussed below in greater detail, the system further includes electronics which generate a qualitative display of the dynamic relative pressure signals over a predetermined portion of the overall video image generated from the mapped composite video signal.

FIG. 2 is a functional block diagram of video pedobarograph electronics 44 shown connected to the force sensor matrix structure 26. The output of amplifier 46 is applied to a video sync stripper 48 and summing/amplification circuitry 50. The amplification circuit 50 may provide linear or logarithmic amplification. The video pedobarograph electronics 44 include a control logic circuit 52 which receives signal outputs from the video sync stripper 48 and from the 16 bit counters 54 as shown. The logic control circuit 52 is electrically connected to and controls operation of the 16 to 1 analog switches 56 which, in turn, receive the dynamic relative pressure signals from the 1,024 sensors of the force sensor mat 26.

The video pedobarograph electronics 44 also include a 4 to 1 analog switch 58 which receives the control input from the control logic circuit 52 and outputs from the 16 to 1 analog switches 56. The output of the 4 to 1 analog switch 58 and the output of the amplifier 46 are combined at circuit 50 to generate the mapped composite video signal at line 34. An amplification circuit 60 is also electrically connected to the force sensor matrix structure 26 as shown in FIG. 2. A 16 to 1 analog switch 61 and the 16 bit counters 54 control application of current sources generated by the amplication circuitry 60 for application to the matrix structure 26. Together, amplification circuitry 60 and amplification circuitry 50 control the gain of the sensors and therefore the intensity of the dynamic relative pressure signals which are mapped to the composite video signal. As shown in FIG. 1, a video gain manual adjustment 51 allows the clinician to control the intensity of the video image to compensate for different levels of force applied to the matrix structure 26. Additionally, a power supply 62 is preferably provided internal to the housing 22.

Figure 3:
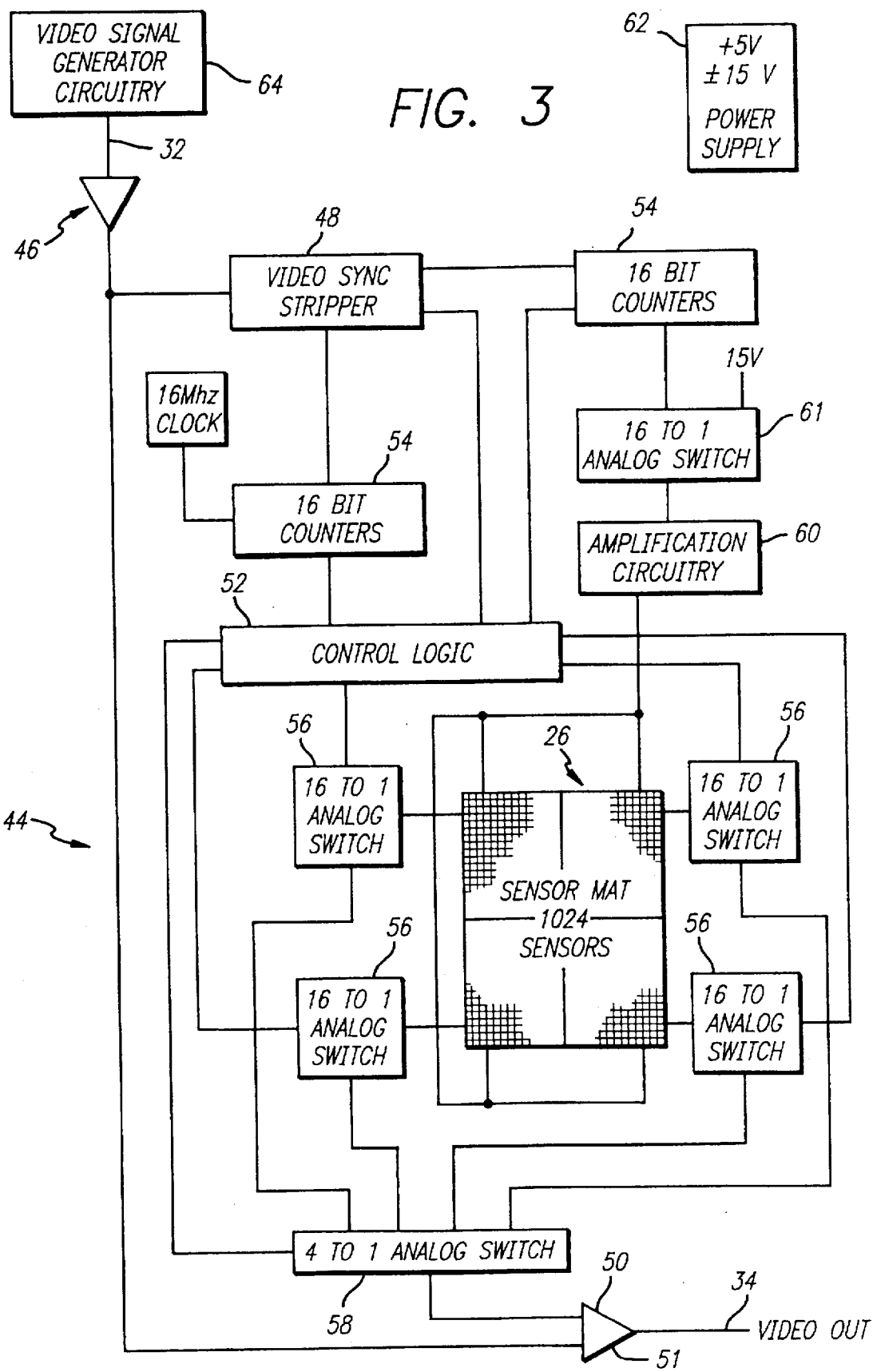
FIG. 3 is an alternative embodiment of the functional block diagram of FIG. 2 further including video signal generator circuitry.

FIG. 3 shows an alternative preferred embodiment of the video pedobarograph electronics 44 which additionally include video signal generator circuitry 64 which provides a composite video signal to the amplifier 46 at line 32. The embodiment of FIG. 3 may be described as a "pressure camera" as a composite video signal of a blank or uniform image is provided at line 32. The video signal generator circuitry 64 may simply and inexpensively be implemented with a programmable video sync generator such as the 74 ACT 715-R manufactured by National Semiconductor and a video sync crystal oscillator such as the 14.31818 MHz RS-170 crystal oscillator/clock.

Figure 4:
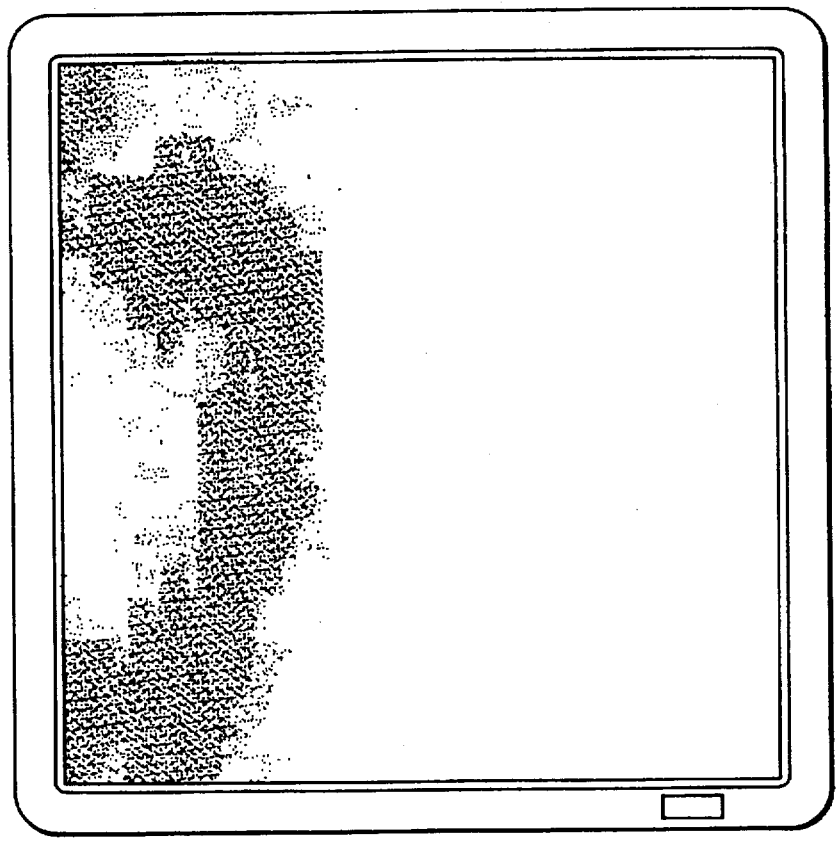
FIG. 4 shows a video image generated from the mapped composite video signal.

FIG. 4 shows a video image at the video display 38 where the control logic 52 has been configured to map the dynamic relative pressure signals over a predetermined portion of the video image covering most of the field of view. Composite video signals may be provided by either the video pedobarograph electronics 44 of FIGS. 2 or 3 in generating such a video image. The external video source 42 may be, but is not necessarily, covered by a lens cap or directed toward a surface which is uniformly illuminated.

Figure 5:
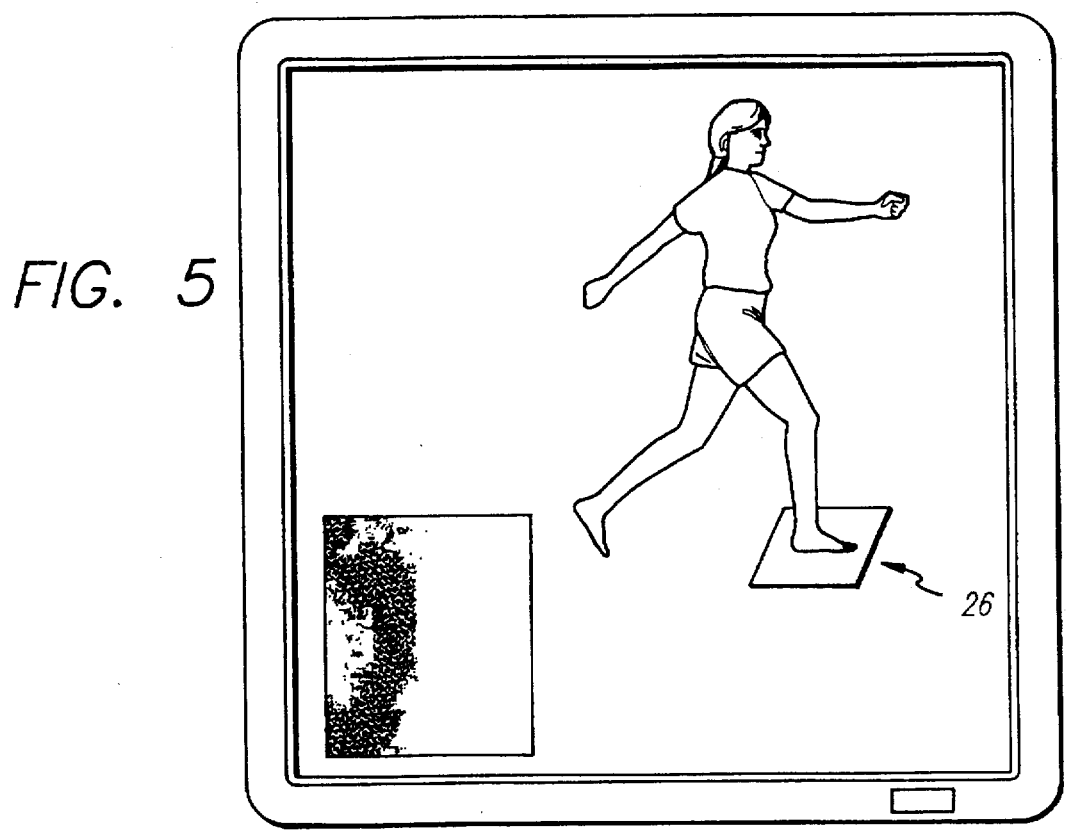
FIG. 5 shows the qualitative display of the dynamic relative pressure signals within a predetermined portion of an overall video image generated from the mapped composite video signal.

FIG. 5 shows an overall video image generated from the mapped composite video signal where the qualitative display of the dynamic relative pressure signals is confined within a predetermined portion of the overall video image. The horizontal and vertical boundaries of the video pedobarograph display within the overall video image are controlled by appropriately configuring the control logic circuit 52 and the 16 bit counters 54. The real time, qualitative display of the dynamic relative pressure signals can thus be correlated with the movement of a person over the force sensor matrix structure 26 by directing the field of view of the external video source 42 toward the person or object applying force to the matrix structure 26.

In conclusion, it is to be understood that the foregoing detailed description and the accompanying drawings illustrate the principals of the invention. However, various changes and modifications may be employed without departing from the spirit and scope of the invention. Thus, by way of example and not of limitation, the video pedobarograph electronics 44 may additionally include pseudo color representation tied to various pressure intensity windows for clinical indication of dangerous dynamic pressure. The size of the force sensor matrix structure 26 and the arrangement and number of the sensors therein may also be modified to accommodate particular applications. Accordingly, the present invention is not limited to the specific form shown in the drawings and described in detail hereinabove.

What is claimed is:

1. A video pedobarograph or foot pressure measuring and display system for providing a real time, qualitative display of dynamic relative pressure measurements, the system comprising:

a plurality of force sensors generating dynamic relative pressure signals, said plurality of force sensors being positioned within a force sensor matrix structure;

a substantially rigid support structure including a substantially planar surface to which said force sensor matrix structure is fixedly secured;

video pedobarograph electronics coupled to said force sensors to receive the dynamic relative pressure signals, said electronics including a video sync stripper for stripping or deriving a video sync signal from a composite video signal received by the video pedobarograph electronics and control logic for directly mapping the dynamic relative pressure signals to the composite video signal in synchronization with the video sync signal to generate a mapped composite video signal; and display means coupled to said electronics for providing a qualitative display of the dynamic relative pressure signals within a predetermined portion of an overall video image generated by said display means from the mapped composite video signal.

2. A video pedobarograph system for mapping dynamic relative pressure measurements to a composite video signal, the system comprising:

a plurality of force sensors generating dynamic relative pressure signals, said plurality of force sensors being arranged in a matrix substantially within a force sensor plane;

a substantially rigid support structure to which said plurality of force sensors are fixedly secured; and video pedobarograph electronics for receiving and directly mapping the dynamic relative pressure signals to a composite video signal in real time to generate a mapped composite video signal.

3. The video pedobarograph system of claim 2 wherein said plurality of force sensors comprise a plurality of force resistors.

4. The video pedobarograph system of claim 2 wherein said plurality of force sensors are fixed in position relative to each other within a force sensor matrix structure.

5. The video pedobarograph system of claim 4 wherein said force sensor matrix structure has a thickness of approximately 20 mils.

6. The video pedobarograph system of claim 4 wherein said substantially rigid support structure includes a substantially planar surface supporting said force sensor matrix structure.

7. The video pedobarograph system of claim 4 wherein said video pedobarograph electronics further include video signal generator circuitry for generating the composite video signal.

8. The video pedobarograph system of claim 7 wherein said video signal generator circuitry includes a programmable video sync generator and a crystal oscillator.

9. The video pedobarograph system of claim 2 wherein said video pedeobarograph electronics further include:
   a video sync stripper for stripping a video sync signal from the composite video signal; and
   control logic for mapping the dynamic relative pressure signals to the composite video signal in synchronization with the video sync signal.

10. The video pedobarograph system of claim 2 wherein the mapped composite video signal comprises a VGA or SVGA signal.

11. The video pedobarograph system of claim 2 further comprising:
    a video display receiving the mapped composite video signal.

12. The video pedobarograph system of claim 2 further comprising:
    a VCR receiving the mapped composite video signal.

13. A video pedobarograph system for mapping dynamic relative pressure measurements to a composite video signal, the system comprising:
    a plurality of force sensors generating dynamic relative pressure signals;
    video pedobarograph electronics for receiving and directly mapping the dynamic relative pressure signals to a composite video signal in real time to generate a mapped composite video signal.

14. The video pedobarograph of claim 13 wherein said plurality of force sensors comprise a plurality of force resistors.

15. The video pedobarograph of claim 13 wherein said plurality of force sensors are fixed in position relative to each other within a force sensor matrix structure.

16. The video pedobarograph of claim 15 wherein said force sensor matrix structure has a thickness of approximately 20 mils.

17. The video pedobarograph of claim 13 further comprising:
    a substantially rigid support structure sized to support said plurality of force sensors substantially within a force sensor plane.

18. The video pedobarograph of claim 13 wherein said video pedobarograph electronics further include video signal generator circuitry for generating the composite video signal.

19. The video pedobarograph of claim 18 wherein said video signal generator circuitry includes a programmable video sync generator and a crystal oscillator.

20. The video pedobarograph of claim 13 wherein the mapped composite video signal comprises a VGA or SVGA signal.

21. The video pedobarograph of claim 13 further comprising:
    a video display receiving the mapped composite video signal.

22. The video pedobarograph of claim 13 further comprising:
    a VCR receiving the mapped composite video signal.

* * * * *